United States Patent [19]

Sollott

[11] 4,284,484

[45] Aug. 18, 1981

[54] PREPARATION OF 1,3,5,7 TETRAACETAMIDO- AND 1,3,5,7-TETRAAMINOADAMANTANES

[75] Inventor: Gilbert P. Sollott, Plymouth Meeting, Pa.

[73] Assignee: The United States of America as represented by the Secretary of the Army, Washington, D.C.

[21] Appl. No.: 167,572

[22] Filed: Jul. 10, 1980

[51] Int. Cl.$^3$ .............................................. B01J 19/12
[52] U.S. Cl. ................................ 204/158 R; 564/414; 564/457
[58] Field of Search .................... 204/158 R; 564/414, 564/457

[56] References Cited

U.S. PATENT DOCUMENTS

| | | | |
|---|---|---|---|
| 3,419,611 | 12/1968 | Moore | 564/125 |
| 3,523,137 | 8/1970 | Moore | 564/125 |
| 3,591,642 | 7/1971 | Szinai et al. | 204/158 R |
| 3,985,803 | 10/1976 | Inamoto et al. | 204/158 N |

OTHER PUBLICATIONS

Stetter et al., Chem. Ber. 93 (1960), p. 1366.

*Primary Examiner*—Howard S. Williams
*Attorney, Agent, or Firm*—Nathan Edelberg; Robert P. Gibson; A. Victor Erkkila

[57] ABSTRACT

1,3,5,7—Tetraacetamidoadamantane is prepared by reacting 1,3,5,7—tetraiodoadamantanewith acetonitrile and water in the presence of actinic radiation. The 1,3,5,7—tetraacetamidoadamantane can be hydrolyzed with hydrochloric acid to produce 1,3,5,7—tetraaminoadamantane tetrahydrochloride, which can be converted to the free base by treatment with an equivalent amount of an alkali, e.g. aqueous sodium hydroxide.

7 Claims, No Drawings

PREPARATION OF 1,3,5,7 TETRAACETAMIDO- AND 1,3,5,7-TETRAAMINOADAMANTANES

GOVERNMENTAL INTEREST

The invention described herein may be manufactured, used and licensed by the Government for Governmental purposes without the payment to me of any royalties thereon.

BACKGROUND OF THE INVENTION—PRIOR ART

The present invention relates to a novel process for preparing 1,3,5,7-tetraacetamidoadamantane, which provides an improved route to 1,3,5,7-tetraaminoadamantane. The latter compound is an intermediate useful for preparing the novel explosive 1,3,5,7 tetranitroadamantane, which is the subject of a copending U.S. patent application of Everett E. Gilbert and Gilbert P. Sollott entitled "1,3,5,7 Tetranitroadamantane and Process for Prepariang Same", Ser. No. 196,956, filed Oct. 14, 1980.

Adamantane is also known by the scientific name of tricyclo [3.3.1.1$^{3,7}$] decane. Adamantanes containing substitutents in the 1,3,5 and 7 positions, as discussed hereinafter, are represented by the following general formula:

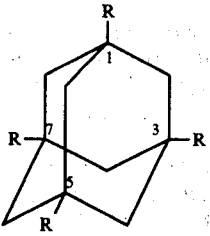

| Compound | R |
|---|---|
| I | H |
| II | Br |
| III | I |
| IV | NHCOCH$_3$ |
| V | NH$_2$ |
| VI | NO$_2$ |

1,3,5,7-Tetraminoadamantane (V) is a known compound, which in the past has been prepared by Hoffmann degradation of 1,3,5,7-adamantanetetracarboxamide produced from 1,3,5,7-adamantanetetracarboxylic acid. However, the tetracarboxylic acid was prepared in very low overall yield by a laborious, multistep procedure involving the Meerwein ester synthesis (H. Stetter and M. Krause, Liebigs Ann. Chem., 717,60 (1968); Tetrahedron Letters, 19,1841 (1967)).

The present invention is directed to a new route for preparing 1,3,5,7-tetraaminoadamantane from 1,3,5,7-tetraiodoadamantane, which makes the compound more readily accessible.

It is known that 1-amino-, 1-acetamido-, 1-toluenesulfamido-, 1-cyano-, and 1-carboxy-adamantanes can be easily prepared by reacting the readily accessible 1-bromoadamantane with ammonia, acetamide, or acetonitrile and sulfuric acid (the latter known as the Ritter reaction), sodium toluenesulfonamide, cuprous cyanide and pyridine, and formic acid in fuming sulfuric acid. resp. These reactions in most cases can be extended to the preparation of the analogous 1,3-disubstituted compounds. However, attempts to prepare the analogous 1,3,5,7-tetrasubstituted adamantanes by the same types of reactions from the readily accessible 1,3,5,7-tetrabromoadamantane (II) have not been successful. Thus, Stetter and Krause (ibid) reported that they were unable to prepare 1,3,5,7-tetracarboxy—and 1,3,5,7-tetraacetamidoadamantanes (IV) in this manner. Similarly, E.E. Gilbert (U.S. Army Armament Research and Development Command, Large Caliber Weapons Systems Laboratory, Dover, N.J.) has been unable to prepare 1,3,5,7-tetraaminoadamantane and the corresponding tetracyano—and tetrakis (toluenesulfonamido) compounds from the tetrabromo compound.

E.E. Gilbert, like Stetter and Krause, has found that 1,3,5,7-tetrabromoadamantane does not undergo the Ritter reaction. In the Ritter reaction, a carbonium ion, generated, for example, from mono- or dibromoadamantane with concentrated sulfuric acid with or without silver sulfate present, interacts with a nitrile, and the nitrilium ion thus formed is converted by water to the amide. (Stetter and Krause, loc. cit. T. Sasaki, S. Eguchi, and T. Toru, Bull. Chem. Soc. Japan, 41,236 (1968), and refs. cited therein.)

An attempted reaction of 1,3,5,7-tetraiodoadamantane (II) under similar conditions was also unsuccessful.

SUMMARY AND DETAILED DESCRIPTION OF THE INVENTION

I have found surprisingly that 1,3,5,7-tetraacetamidoadamantane can be obtained in good yield by reacting 1,3,5,7-tetraiodoadamantane, obtainable in high yield from the corresponding tetrabromo compound by halogen exchange (see J.W. McKinley, R.E. Pincock and W.B. Scott, J. Am. Chem. Soc. 95, 2030 (1973), with acetcnitrile and water in the presence of actinic radiation, i.e. photochemically. It is considered surprising to find that the tetraiodoadamantane compound undergoes a photochemically initiated Ritter-Type reaction with acetonitrile to produce the tetraacetamide, particularly since it does not undergo the sulfuric acid-catalyzed Ritter reaction. Perkins and Pincock (Tetrahedron Letters, 943 (1975); Perkins, Dissertation (Univ. British Columbia) 1976) had previously reported that the mono.-and diacetamido derivatives are formed in high yields by the photolysis of 1-iodo- and 1,3-diiodoadamantanes in alkyl nitrile solvents according to the following reaction shown for the monosubstituted product, wherein Ad signifies the adamantyl radical:

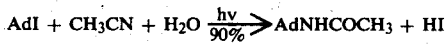

The reaction is mechanistically similar to the Ritter reaction (See Perkins and Pincock, loc. cit.). I have obtained 1-acetamidoadamantane from the 1-bromo compound photochemically in this manner, as expected. However an attempt to carry out the reaction in similar manner with 1,3,5,7-tetrabromoadamantane for the preparation of the tetraacetamidoadamantane was unsuccessful. Only monoacetamido(tribromo)adamantane was obtained. This lack of sufficient reactivity of 1,3,5,7-tetrabromoadamantane in the photochemical reaction is in keeping with its inability to react and form other tetrasubstituted adamantane derivatives noted previously. The formation of 1,3,5,7-tetraacetamidoadamantane from the tetraiodo compound (III) photochemically is even more surprising in view of the fact that reactions which fail to occur with 1,3,5,7-tetrabromoadamantane (II) noted above, generally also fail to occur in the case of the 1,3,5,7-tetraiodo compund (III).

The tetraacetamido compund (IV) thus formed can be hydrolyzed with hydrochloric acid to 1,3,5,7-tetraaminoadamantane tetrahydrochloride in over 80% yield, from which the base can be liberated by treatment with alkali, e.g. sodium hydroxide.

Accordingly, the present invention provides a novel process for preparing 1,3,5,7-tetraacetamido- an tetraaminoadamantanes via an overall route which starts from adamantane and proceeds via the following compounds, all of which are obtained in reasonable yields:

The following examples illustrate specific embodiments of the method of carrying out the process of the present invention.

EXAMPLE 1.

Preparation of 1,3,5,7-Tetraacetamidoadamantane.

In a one liter quartz reaction flask equipped with a condenser and agitator, 1,3,5,7-tetraiodoadamantane (7.7 g=0.012 mole) was stirred briskly in 800 ml of acetonitrile (0.07–0.1% water content) to which 1.0 ml of water had been added. The resulting mixture was photolyzed for 64 hours at approximately 60° C. (ambient temperature) in a Rayonet Photochemical Reactor containing 16 lamps, each lamp approximately 0.03 watt, 1849 angstroms and 2.2 watts, 2537 angstroms (manufacturer's literature-The Southern New England Ultraviolet Co., Middletown, CT). The reaction mixture was filtered to separate the yellowish solids formed, which were then washed with acetonitrile and air-dried. The deep-red acetonitrile filtrate was flash vaporized to remove the acetonitrile. The dark, tarry residue was dissolved in tetrahydrofuran and the pale yellow solids which remained undissolved therein were separated by filtration, washed with tetrahydrofuran solvent and air-dried. The combined solids were dissolved in hot water and the solution was neutralized with aqueous sodium hydroxide and filtered. The filtrate was flash evaporated to dryness. The residue of white solids was washed first with acetone, then with cold water, and finally with acetone and air dried. 2.68 grams of 1,3,5,7-tetraacetamidoadamantane product were thus obtained, corresponding to a yield of 51% of theory based on the tetraiodo starting material.

The product crystallized from water in the form of needles and analyzed as the tetrahydrate. It showed no melting to 360° C., which agrees with that reported by Stetter and Krause (loc. cit.). Analysis. Calculated for $C_{18}H_{28}N_4O_4 \cdot 4H_2O$: C, 49.53; H, 8.31; N, 12.84; O, 29.32; $H_2O$ 16.51%; Mol. wt. 436.5. Found. C, 49.97; H, 8.50; N, 12.46; O, 29.33; $H_2O$ (by weight loss). 16.23%; Mol. wt. (in $H_2O$), 421.

EXAMPLE 2

Preparation of 1,3,5,7-Tetraaminoadamantane Tetrahydrochloride 1,3,5,7-Tetraacetamidoadamantane tetrahydrate (2.0 g=4.6 mmoles) was dissolved in 18% hydrochloric acid (30 ml of concentrated hydrochoric acid diluted with 30 ml of water) and the solution was refluxed for three hours. The crystalline product thus obtained was separated from the mixture by filtration, washed with acetone and dried. 1.29 g of product, mp.>360° C., in agreement with that reported by H. Stetter and C. Wulff, Chem. Ber., 93,1366 (1960), corresponding to an 82% yield, were obtained. Analysis. calculated for $C_{10}H_{20}H_4 \cdot 4HCl$: C, 35.11; H, 7.07; N, 16.38. Found, C, 34.45; H, 7.17; N, 16.01.

The tetrahydrochloride salt can be readily converted to the free base, 1,3,5,7-tetraaminoadamantane, by treatment with an alkali; e.g. aqueous sodium hydroxide.

EXAMPLE 3

1,3,5,7-Tetraiodoadamantane, employed as starting material in Example 1, was prepared according to the process described by J. W. McKinley et al., J. Am. Chem. Soc. 95, 2030 (1973). Bromine (1.3 ml; 0.025 mole) was added to small pieces of aluminum foil (20.0 g; 0.074 g-atom) in methylene iodide (240 ml), and the mixture stirred for 35 min in a bath at 80° C. 1,3,5,7-Tetrabromoadamantane (20.0 g; 0.044 mole) was added in one portion and allowed to react for 15 min at the same temperature. The reaction mixture was poured into 400 ml of cold water with stirring, and sodium bisulfite was added to remove the color of bromine. The methylene iodide phase was separated, washed with water, and the solvent flash-evaporated. The solid residue was washed with chloroform, then with acetone. Recrystallization from toluene yielded 21.2 g (75%), in the form of needles, mp 370°–371° C. dec (lit. 370° C. dec).

EXAMPLE 4

1,3,5,7-Tetrabromoadamantane, employed as starting material in Example 3, was prepared by a modification of the procedure of A. P. Khardin, I. A. Novakov and S. S. Radchenko, Zh. Org. Khim., Eng. Ed., 9,435 (1973) as follows:

Adamantane (27.0 g; 0.2 mole) was added portionwise over 30 min to a stirred mixture of bromine (350 g; 2.2 moles) and anhydrous aluminum chloride (27.0 g; 0.2 mole) at 5°–10° C. The mixture was then heated to 70° over a period of 1 hr, and held at that temperature for 24 hr. Hydrogen bromide was evolved copiously during the addition and heating. Excess bromine (180 g) was distilled on the water bath. The residue was triturated with aqueous sodium sulfite (to remove excess bormine) with added hydrochloric acid (to dissolve aluminum salts). The solids were removed by filtration, washed and air dried, and weighed 91 g. Recrystallization from 1200 ml of glacial acetic acid gave 52.0 g (58%) of tan, powdery product, mp 245°–247° C. (lit. 246°–247° C.) Addition of 100 ml of water to the filtrate gave 10.3 g, mp 235°–240° C. The IR spectra of both crops were identical.

The process of the present invention for preparing 1,3,5,7-tetraacetamidoadamantane comprises reacting a mixture of 1,3,5,7-tetraiodoadamantane, acetonitrile and water in the presence of actinic radiation and thereafter separating the tetraacetamido compound formed. Four moles each of acetonitrile and water per mole of tetraiodoadamantane are theoretically required for the reaction. However, the acetonitrile is usually employed in large excess over this amount to serve as the solvent for the reaction mixture. The present process can be carried out at temperatures within the range of about 40° C. to about the boiling temperature of the reaction mixture at ordinary pressure, e.g. about 82° C. Higher temperatures can be employed but require carrying out the process under superatmospheric pressure, while the use of lower temperature results in slower reaction rates and hence is less preferred. The present process can be effected in the presence of actinic radiation having a wavelength with the range of about 1800 and 2600 angstroms but is not limited thereto. Higher wattage ultra-violet sources, for example 100 watts and higher, are also expected to be useful for effecting the present process.

The 1,3,5,7-tetraacetamidoadamantane product thus obtained in 51% yield can be hydrolyzed with 18% hydrochloric acid to 1,3,5,7-tetraaminoadamantane, which can be isolated in yields as high as 82% as the tetrahydrochloride. The tetrahydrochloride salt can be readily converted to the free base by treatment with an equivalent amount of an alkali, using, for example, 10% aqueous sodium hydroxide. The hydrolysis of 1,3,5,7-tetraacetamidoadamantane to the corresponding tetraamino compound is also novel, although hydrochloric acid is known to hydrolyze 1,3-diacetamidoadamantane to 1,3-diaminoadamantane (H. Stetter and C. Wulff, Chem. Ber. 93, 1366 (1960). However, when this reaction is applied to 1-acetamidoadamantane, the only product obtained is 1-chloroadamantane in 98% yield (H. Stetter, M. Schwarz and A. Hirschhorn, Chem. Ber. 92, 1629 (1959).

The foregoing disclosure is merely illustrative of the principles of this invention and is not to be interpreted in a limiting sense. I wish it to be understood that I do not desire to be limited to the exact details described because obvious modifications will occur to a person skilled in the art.

I claim:

1. A process for preparing 1,3,5,7-tetraacetamidoadamantane, which comprises reacting 1,3,5,7-tetraiodoadamantane with acetonitrile and water in the presence of actinic radiation.

2. A process according to claim 1, wherein the actinic radiation has a wavelength between about 1800 angstroms and 2600 angstroms.

3. A process according to claim 1, wherein at least 4 moles of acetonitrile and at least 4 moles of water are present per mole of 1,3,5,7-tetraiodoadamantane.

4. A process according to claim 1, wherein the acetonitrile is employed as the reaction solvent.

5. A process according to claim 1,2,3, or 4, wherein the reaction temperature is within the range of about 40° C. to 82° C.

6. A process for preparing 1,3,5,7-tetraaminoadamantane which comprises reacting 1,3,5,7-tetraiodoadamantane with acetonitrile and water in the presence of actinic radiation to form 1,3,5,7-tetraacetamidoadamantane and hydrolyzing the 1,3,5,7-tetraacetamidoadamantane with hydrochloric acid to form 1,3,5,7-tetraaminoadamantane tetrahydrochloride.

7. A process according to claim 6, wherein the 1,3,5,7-tetraaminoadamantane tetrahydrochloride is reacted with an alkali to form 1,3,5,7-tetraaminoadamantane.

* * * * *